United States Patent [19]

Leyshon et al.

[11] Patent Number: 5,021,333
[45] Date of Patent: Jun. 4, 1991

[54] COLOR PHOTOGRAPHIC ELEMENT, COMPOUNDS AND PROCESS

[75] Inventors: Llewellyn J. Leyshon, Watford, United Kingdom; Paul R. Buckland; Paul A. Burns, both of Rochester, N.Y.

[73] Assignee: Eastman Kodak Company, Rochester, N.Y.

[21] Appl. No.: 572,927

[22] Filed: Aug. 24, 1990

[30] Foreign Application Priority Data

Sep. 5, 1989 [GB] United Kingdom ............... 8920059
Nov. 2, 1989 [GB] United Kingdom ............... 8924665

[51] Int. Cl.$^5$ .............................................. G03C 7/36
[52] U.S. Cl. ..................................... 430/551; 430/557
[58] Field of Search ................... 430/556, 557, 551

[56] References Cited

U.S. PATENT DOCUMENTS

| | | | |
|---|---|---|---|
| 2,875,057 | 2/1959 | McCrossen et al. | 430/556 |
| 3,408,194 | 10/1968 | Loria | 430/557 |
| 4,203,768 | 5/1980 | Inouye et al. | 430/389 |
| 4,230,851 | 10/1980 | Renner et al. | 430/556 |
| 4,388,403 | 6/1983 | Helling et al. | 430/546 |
| 4,510,234 | 4/1985 | Matsuzaka et al. | 430/557 |
| 4,617,256 | 10/1986 | Kunitz et al. | 430/557 |
| 4,770,983 | 9/1988 | Ogawa et al. | 430/557 |
| 4,770,987 | 9/1988 | Takahashi et al. | 430/551 |
| 4,783,397 | 11/1988 | Ogawa et al. | 430/551 |
| 4,833,070 | 5/1989 | Kunitz et al. | 430/557 |

FOREIGN PATENT DOCUMENTS 0267491 10/1987 European Pat. Off.

*Primary Examiner*—Richard L. Schilling
*Attorney, Agent, or Firm*—Richard E. Knapp

[57] ABSTRACT

A photographic yellow dye-forming coupler is represented by the formula:

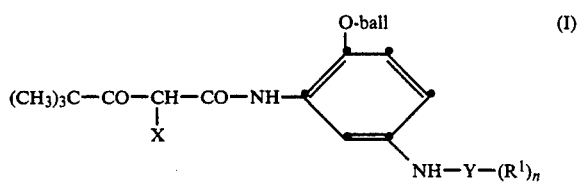

(I)

wherein:
  $R^1$ is alkyl of 1 to 4 carbon atoms;
  ball is a ballast group of such size and configuration as to render the coupler nondiffusible in a photographic element;
  Y is CO, $PO_3$ or $SO_2$;
  X is an aryloxy coupling-off group; and
  n is 1 or, when Y is $PO_3$, n is 2.

Such a coupler is useful in a color photographic silver halide element and process to provide improved activity.

8 Claims, No Drawings

COLOR PHOTOGRAPHIC ELEMENT, COMPOUNDS AND PROCESS

This invention relates to photographic yellow couplers, photographic materials containing them, a method for their preparation and intermediates therefor.

Yellow dye-forming couplers of the pivaloylacetanilide class are well-known. U.S. Pat. No. 3,408,194 describes such couplers. Two couplers of this type in commercial use have the following structural formulae:

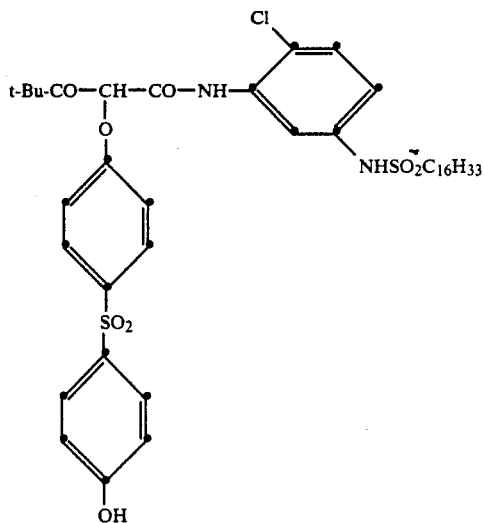

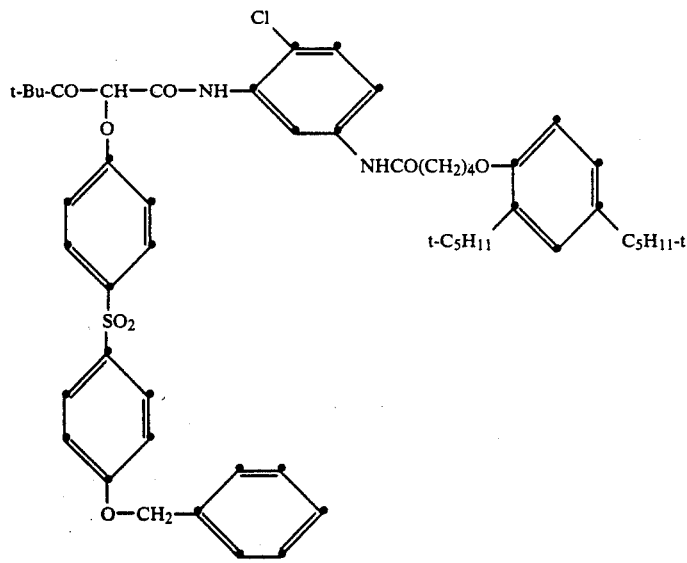

Coupler (A) has good reactivity but the yellow dye produced has a poor hue having unwanted absorption in the green portion of the spectrum. Coupler (B) has a better hue but is much less reactive than coupler (A).

U.S. Pat. No. 4,388,403 describes polymeric dispersions on which photographic couplers may be carried. A number of individual couplers are disclosed which provide yellow, cyan or magenta dyes and among these is coupler Y10 having the formula:

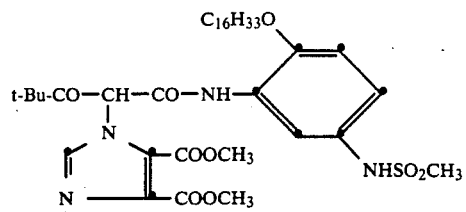

However, there is no description of the preparation or use of this compound.

According to the present invention, there is provided (A)

(B)

a color photographic element comprising a support bearing at least one photographic silver halide emulsion and a yellow dye-forming coupler of the formula:

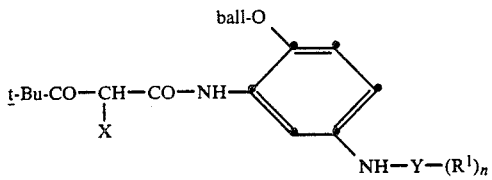

(I)

wherein:
$R^1$ is an alkyl group of 1–4 carbon atoms,
ball is a ballast group of such size and configuration as to render the coupler nondiffusible in photographic layers,
Y is CO, $PO_3$ or $SO_2$,
X is an aryloxy coupling-off group, and
n is 1 or, when Y is $PO_3$, n is 2.
t-Bu herein is a t-butyl group.

The couplers of the present invention have improved hue compared with coupler (A) and improved activity compared with coupler (B) without any loss of other desirable properties.

The ballast group preferably comprises alkyl and/or aryl moieties optionally linked by ether or ester groups. In a preferred group of couplers, the ballast group comprises an aryl moiety substituted with one or more alkyl groups, e.g., alkyl groups containing 4–10 carbon atoms. Such couplers are less expensive to produce than their nonaromatic analogues. Examples of ballast groups which may be employed are:

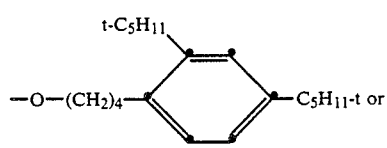

The coupling-off group X may be a phenoxy group optionally substituted with alkyl or arylsulphonyl, alkylsulphonamido, or alkoxycarbonyl groups which themselves are optionally substituted. Preferred coupling-off groups are phenoxy groups containing electron-withdrawing substituents at the ortho- and/or para-positions, especially at the para-and one ortho-position. In addition, ionizable substituents are also beneficial. Examples of coupling-off groups which may be used are the following:

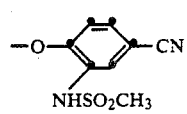
(a)

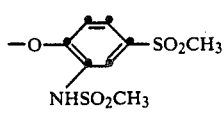
(b)

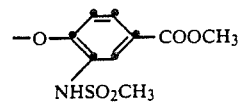
(c)

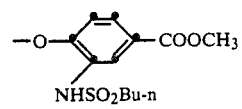
(d)

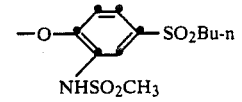
(e)

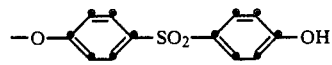
(f)

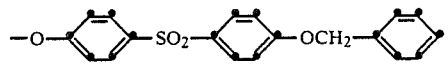
(g)

or

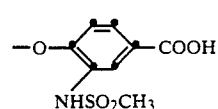
(h)

Examples of couplers according to the present invention are listed in the following Table.

TABLE 1

(I)

t-Bu-CO—CH(X)—CO—NH—[aryl with R]—NH—Y—$R^1$

| Coupler | $R^1$ | R | Y | X |
|---|---|---|---|---|
| 1 | $CH_3$ | $-O-CH_2COOC_{12}H_{25}$-n | $SO_2$ | (b) |
| 2 | " | $-O-$⟨phenyl⟩$-$Octyl-t | $SO_2$ | (f) |
| 3 | " | $-O-$⟨phenyl⟩$-$Octyl-t | $SO_2$ | (c) |
| 4 | " | $-O-CH(n-C_{10}H_{21})COOCH_3$ | $SO_2$ | (b) |
| 5 | " | $-O-$⟨phenyl⟩$-$Bu-t | CO | (b) |
| 6 | " | $-O-(CH_2)_4-O-$⟨phenyl with t-pentyl, pentyl-t⟩ | $SO_2$ | (b) |

Comparative couplers of the prior art employed in the Examples below are listed in Table 2 below.

TABLE 2

$$\text{t-Bu-CO—CH—CO—NH—} \underset{X}{\overset{R^3}{\bigcirc}} \text{—NH—R}^4 \quad (I)$$

| Coupler | $R^4$ | $R^3$ | X |
|---|---|---|---|
| A | $-SO_2C_{16}H_{33}$-n | Cl | (f) |
| B | $-CO(CH_2)_4O-\text{(2,4-di-t-pentylphenyl)}$ | Cl | (g) |
| C | $-SO_2C_{16}H_{33}$-n | $-OCH_3$ | (f) |
| D | $-CO(CH_2)_4O-\text{(2,4-di-t-pentylphenyl)}$ | Cl | (h) | with a phenol ($R^2$—OH) and reducing the nitro group of the resulting compound to form a compound of the formula:

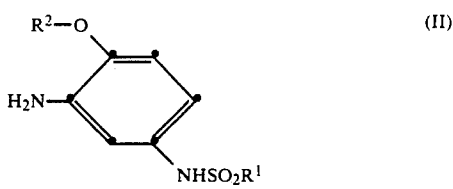

wherein:
$R^2$ is an aryl group which is optionally substituted, for example, with one or more alkyl groups, and
$R^1$ is an alkyl group of 1-4 carbon atoms.

It is noted that Matsuo et al, *Chem. Pharm. Bull.*, 1985, 33, (10), 4409–21, describes compounds of formula (II) above wherein $R^2$ is an unsubstituted aryl group.

The full reaction scheme including the above steps is as follows:

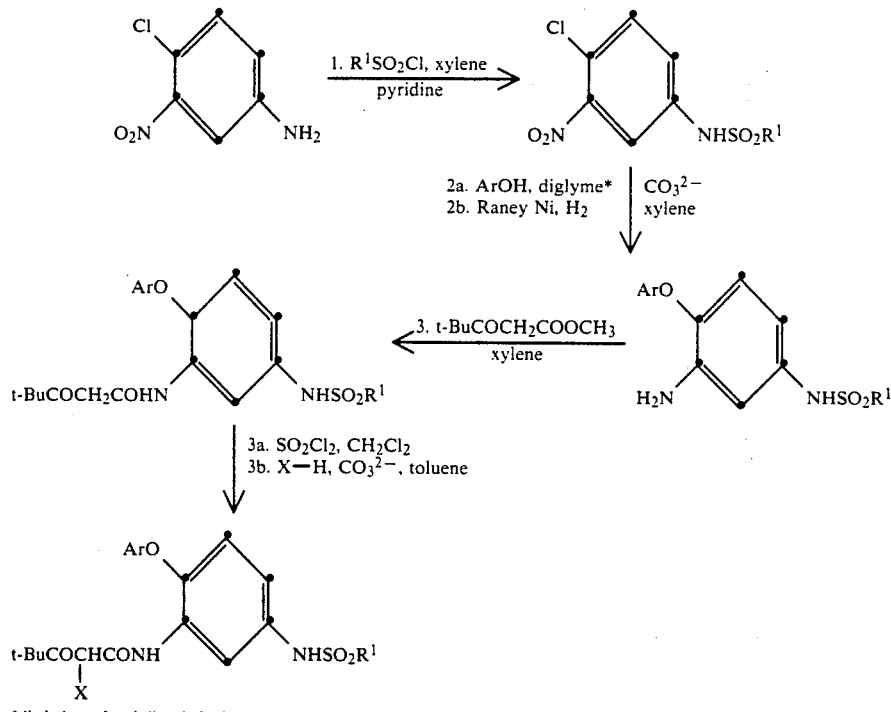

*diethylene glycol dimethyl ether

The present couplers may have associated therewith a dye stabilizer of the blocked bis-phenol type, for example, those described in U.S. Pat. No. 4,782,011 and particularly Compound 11 described therein.

The present couplers having aryl ballast groups may be prepared by a method which includes the step of condensing a compound of the formula:

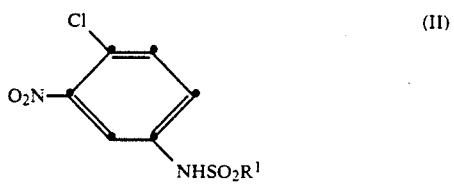

Couplers of the present invention in which the ballast group is other than aryl may be prepared by methods, in themselves, known.

The invention further provides compounds of formula III wherein $R^2$ is an aryl group substituted with one or more alkyl groups as novel intermediates.

The dye-forming couplers of this invention can be used in the ways and for the purposes for which dye-forming couplers have been previously used in the photographic art.

Typically, the couplers are associated with a silver halide emulsion layer coated on a support to form a photographic element. As used herein, the term "associated with" signifies that the coupler is incorporated in the silver halide emulsion layer or in a layer adjacent thereto where, during processing, it is capable of reacting with silver halide development products.

Typically, the coupler is dissolved in a coupler solvent and this solution is dispersed in an aqueous gelatin solution. Examples of coupler solvents which may be used are dibutyl phthalate, tricresyl phosphate, diethyl lauramide and 2,4-di-tertiary-amylphenol. In addition, an auxiliary coupler solvent may also be used, for example, ethyl acetate, cyclohexanone and 2-(2-butoxyethoxy)ethyl acetate, which are removed from the dispersion before incorporation into the photographic material.

The photographic elements can be single-color elements or multicolor elements. In a multicolor element, the yellow dye-forming couplers of this invention would usually be associated with a blue-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the elements, including the layers of the image-forming units, can be arranged in various orders as known in the art.

A typical multicolor photographic element comprises a support bearing a yellow dye image-forming unit comprised of at least one blue-sensitive silver halide emulsion layer having associated therewith at least one yellow dye-forming coupler being a coupler of this invention, and magenta and cyan dye image-forming units comprising at least one green- or red-sensitive silver halide emulsion layer having associated therewith at least one magenta or cyan dye-forming coupler, respectively. The element can contain additional layers such as filter layers.

In the following discussion of suitable materials for use in the emulsions and elements of this invention, reference will be made to *Research Disclosure*, Dec., 1978, Item 17643, published by Industrial Opportunities, Ltd., The Old Harbourmaster's, 8 North Street, Emsworth, Hants P010 7DD, U.K. This publication will be identified hereafter as "*Research Disclosure*".

The silver halide emulsion employed in the elements of this invention can be either negative-working or positive-working. Suitable emulsions and their preparation are described in *Research Disclosure* Sections I and II and the publications cited therein. Suitable vehicles for the emulsion layers and other layers of elements of this invention are described in *Research Disclosure* Section IX and the publications cited therein.

In addition to the couplers of this invention, the elements of the invention can include additional couplers as described in *Research Disclosure* Section VII, paragraphs D, E, F and G, and the publications cited therein. The couplers of this invention and any additional couplers can be incorporated in the elements and emulsions as described in *Research Disclosure* Section VII, paragraph C, and the publications cited therein.

The photographic elements of this invention or individual layers thereof can contain brighteners (see *Research Disclosure* Section V), antifoggants and stabilizers (see Research Disclosure Section VI), antistain agents and image dye stabilizer (see *Research Disclosure* Section VII, paragraphs I and J), light-absorbing and -scattering materials (see *Research Disclosure* Section VIII), hardeners (see *Research Disclosure* Section XII), plasticizers and lubricants (see *Research Disclosure* Section XIII), matting agents (see *Research Disclosure* Section XVI) and development modifiers (see *Research Disclosure* Section XXI).

The photographic elements can be coated on a variety of supports as described in *Research Disclosure* Section XVII and the references described therein.

Photographic elements can be exposed to actinic radiation, typically in the visible region of the spectrum, to form a latent image as described in *Research Disclosure* Section XVIII and then processed to form a visible dye image as described in *Research Disclosure* Section XIX. Processing to form a visible dye image includes the step of contacting the elements with a color-developing agent to reduce developable silver halide and oxidize the color-developing agent. Oxidized color-developing agent in turn reacts with the coupler to yield a dye.

Preferred color-developing agents are p-phenylenediamines. Especially preferred are 4-amino-3-methyl-N,N-diethylaniline hydrochloride, 4-amino-3-methyl-N-ethyl-N-$\beta$-(methylanesulphonamido)ethylaniline sulphate hydrate, 4-amino-3-methyl-N-ethyl-N-$\beta$-(methanesulphonamido)ethyl-N,N-diethylaniline hydrochloride and 4-amino-N-ethyl-N-(2-methoxyethyl)-*m*-toluidine di-*p*-toluene sulphonate.

With negative-working silver halide emulsions, this processing step leads to a negative image. To obtain a positive (or reversal) image, this step can be preceded by development with a nonchromagenic developing agent to develop exposed silver halide, but not form dye, and then uniform fogging of the elements to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The invention is illustrated by the following Examples in which "petrol" means petroleum ether (bp 60°–80° C.) and in which all temperatures are in degrees Celsius.

EXAMPLE 1

(a) N-(4-chloro-3-nitrophenyl)methanesulphonamide

Methanesulphonyl chloride (58.3 g, 0.509 mole) was added in one portion to a stirred solution of 97% 4-chloro-3-nitroaniline (86 g, 0.485 mole) in pyridine (80 ml) and xylene (500 ml). The temperature rose to 50° and the mixture was allowed to stand for a further 2 hr before addition of a mixture of 10M-hydrochloric acid (100 ml) and water (100 ml). The brown solid which was collected and washed successively with xylene (50 ml) and water (3 × 50 ml). The damp material was crystallized from methanol (800 ml) to give a solid which was collected, washed with methanol (2 × 50 ml) and dried to give the product 95 g (78%) m.p. 163°.

(b) N-[4-(4-*t*-butylphenoxy)-3-aminophenyl]methane sulphonamide

N-(4-chloro-3-nitrophenyl)methanesulphonamide (50 g, 0.2 mole), 4-*t*-butylphenol (33 g, 0.22 mole), potassium carbonate (62.1 g, 0.45 mole) and diglyme (50 ml) were heated and stirred at 165°–170° for 24 hr. The mixture was cooled to 110° and xylene (150 ml) followed by a mixture of 10M-hydrochloric acid (55 ml) and water (130 ml) added.

After stirring for 0.5 hr at 70°, the layers were allowed to separate and the aqueous solution discarded. The xylene solution was washed with hot (60°) 1M-hydrochloric acid (50 ml) and then made up to 400 ml by addition of more xylene. The resulting solution of N-[4-(4-t-butylphenoxy)-3-nitrophenyl]methanesulphonamide and wet Raney nickel (10 g) were introduced into an autoclave and heated without stirring in an atmosphere of hydrogen to an initial pressure of 36 atmospheres and an initial temperature of 50°. Heating was stopped and stirring commenced, which caused the temperature to rise to 95° and the pressure to drop to 25 atmospheres over 15 min. After 2 hr, the mixture was cooled and precipitated material and catalyst collected by filtration. The solids were washed with xylene and the damp material dissolved in warm tetrahydrofuran (200 ml) followed by filtration to remove catalyst. After removal of most of the solvent, the residue was slurried with ethanol (100 ml) and the solid collected, washed with ethanol (2×25 ml) and dried to give the product 41.2 g (61%).

(c) Coupler of formula (I) [X=H, ball-O-=4-t-butylphenoxy, R¹=Me, Y=SO₂]

N-[4-(4-t-butylphenoxy)-3-aminophenyl]methanesulphonamide (33.4 g, 0.1 mole), methyl pivaloylacetate (17.4 g, 0.11 mole) and xylene (50 ml) were heated under reflux. After 1 hr, more xylene (50 ml) was added and then 50 ml of distillate removed. This was repeated at 1-hr intervals over 5.5 hr. Finally, xylene (20 ml) was removed and acetic acid (200 ml) added to the hot liquors. After leaving to stir overnight, the solid material was collected and washed successively with acetic acid (2×30 ml) and 40°-60° petrol (3×50 ml) before drying to give the product 37.4 g (81%) m.p. 189°.

(d) Coupler of formula (I) [X=Cl, ball-O-=4-t-butylphenoxy, R¹=Me, Y=SO₂]

Coupler (1, X=H, ball-O-=4-t-octylphenoxy, R¹=Me; 20.64 g, 0.04 mole) was dissolved in boiling dichloromethane (200 ml), the solution cooled and sulphuryl chloride (5.4 g, 0.04 mole) in dichloromethane (20 ml) added in portions over 3 min. After 0.5 hr, the solution was evaporated to c.a. 40 ml and 40°-60° petrol (100 ml) added with gentle heating. The solution was cooled with stirring and the solid obtained was collected, washed with petrol and dried at 40° under vacuo to give the product as a white solid 19.4 g (88%), m.p. 157°.

Intermediate (d) can be converted into a coupler of the present invention as illustrated in Example 2.

EXAMPLE 2

(a) Coupler of formula (I)
[X=4-(4-benzoyloxyphenylsulphonyl)phenoxy, ball-O-=4-t-octylphenoxy, R¹=Me, Y=SO₂]

A mixture of sulfonyldiphenol monobenzyl ether (10.38 g, 0.0305 mole), the chloro coupler [X=Cl, ball-O=4-t-octylphenoxy, R¹=Me, Y=SO₂] (16.0 g, 0.0291 mole) and toluene (40 ml) was stirred and heated to 65°. Warm water (8 ml) was added followed by aliquat 336 (0.81 g) in toluene (3 ml). The temperature was then raised to 70° over a 20-min period and sodium carbonate (1.8 g) in water (7 ml) added over 10 min between 70°-75° with rapid stirring (260 rpm). Rapid stirring was maintained and the mixture kept at 75°-80° for a further 2 hr. More sodium carbonate (0.9 g) was added and the mixture stirred and heated for a further 2 hr.

The layers were separated at 70° and the pH of the aqueous layer checked and found to be pH 9. The orange toluene solution was washed successively with hot (70°) water (15 ml) and hot (70°) water (15 ml) containing citric acid (0.3 g). The toluene was removed at 90° on a Rotavapor over 1 hr to give a solid foam which, after addition of petrol, was stirred overnight to give a yellow solid. This material was collected by fitration, washed with petrol (5×25 ml) and dried to give crude product 25.7 g, (100%). This material was extremely soluble in all common solvents except petrol and, despite many attempts, failed to crystallize from various solvent mixtures containing petrol. A purified sample required for photographic evaluation was obtained as a solid foam after column chromatography (2:1 petrol:ethyl acetate), followed by treatment with diethyl ether.

Found: C, 66.2; H, 6.2; N, 2.8; S, 7.6. C₄₇H₅₄N₂O₉S₂ requires: C, 66.0; H, 6.4; N, 3.3; S, 7.6%.

(b) Coupler (2) of formula (I)
[X=4-(4-hydroxyphenylsulphonyl)phenoxy, X=4-t-octylphenoxy, R¹=Me, Y=SO₂]

The product of (a) above (8.0 g, c.a. 9.36 mmole), 2-propanol (240 ml) and 10% Pd-C (3 g) were introduced into an autoclave and heated without stirring in an atmosphere of hydrogen to an initial pressure of 33 atmospheres and an initial temperature of 55°. Stirring was begun which caused the temperature to rise to 65° and the pressure to fall by 1.8 atmospheres over a 3-hr period. The catalyst was removed and the solution evaporated to give a syrup which was dissolved in ether, and the solution evaporated to give a solid foam 6.4 g (90%). This material was extremely soluble in all common solvents except petrol and, despite many attempts, failed to crystallize from various solvent mixtures containing petrol.

Found: C, 62.3; H, 6.4; N, 3.1; S, 8.5. C₄₀H₄₈N₂O₉S₂ requires: C, 62.8, H, 6.3; N, 3.7; S, 8.4%.

EXAMPLE 3

The couplers identified below were coated in a monochrome format with a blue-sensitive silver chloride emulsion at the indicated coating weights and exposed and processed through RA4 chemistry. The coatings were assessed sensitometrically and the hue of the image dyes and their stability to heat and light measured.

The results of these tests are summarized in Table 3 below. Data from three separate coating experiments are included, and in each experiment the couplers of the present invention are compared with the two prior-art couplers (A) and (B). In some cases, a light stabilizer compound of the formula:

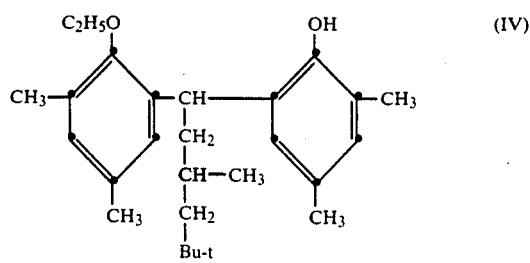
(IV)

was incorporated in the coupler dispersion at a level equal to half the weight of coupler.

In the Table, the coupler is identified in column 2 while column 3 shows the coverages (in g/m$^2$) of coupler and silver in the coating. Column 4 (gamma) gives the sensitometric contrast of the coatings and column 5 [Dg (1.5)] is a measure of the color purity of the image. The quoted figure is the green density of the image corresponding to a blue density of 1.5 (status A filtration). Thus, low values indicate least contamination of the image hue. The last two columns [HID (1.0) and DOF (1.0)] indicate the light and dark stability of the image dye. The quoted figures are the changes in density from an initial value of 1.0 for a 3-wk exposure to a UV-filtered xenon arc at 50 klux (HID) and a 10-day dark incubation at 85° C., 45% RH (DOF).

TABLE 3

| Expt. No. | Coup. | Coup/Ag mg/m$^2$ | gamma | Dg (1.5) | HID (1.0) | DOF (1.0) |
|---|---|---|---|---|---|---|
| 1 | A* | 592/247 | 2.95 | 0.35 | −0.22 | −0.11 |
|  | 1 | 592/247 | 3.30 | 0.30 | −0.50 | −0.03 |
|  | 1* | 592/247 | 3.11 | 0.30 | −0.12 | −0.02 |
|  | 4 | 592/247 | 2.98 | 0.31 | −0.31 | nil |
|  | 4 | 592/247 | 2.92 | 0.30 | −0.08 | nil |
|  | B | 1076/270 | 2.78 | 0.29 | −0.29 | −0.11 |
| 2 | A | 538/247 | 3.18 | 0.34 | −0.81 | −0.09 |
|  | 2 | 538/247 | 2.94 | 0.31 | −0.50 | −0.07 |
|  | 2* | 538/247 | 2.98 | 0.31 | −0.18 | −0.05 |
|  | 3 | 538/247 | 0.31 | 3.16 | −0.30 | −0.03 |
|  | B | 1076/270 | 2.63 | 0.29 | −0.19 | −0.12 |
| 3 | A* | 538/215 | 2.89 | 0.32 | −0.23 | −0.10 |
|  | 5* | 510/215 | 2.81 | 0.27 | −0.06 | −0.11 |
|  | B | 1076/270 | 2.82 | 0.30 | −0.29 | −0.12 |

*indicates that the coupler dispersion contains a bisphenol stabilizer of Formula IV above at half the weight of the coupler.

The important features to note in the tabulated data are as follows:

(a) Coupler (A) was always coated at approximately half the coverage of (B) and with lower silver. Nonetheless, the photographic activity as indicated by gamma was higher demonstrating the substantial reactivity advantage for (A).

(b) The hue of image dye from (A) is inferior to that from (B); the unwanted green absorption is consistently significantly higher.

(c) The couplers of the present invention were coated at coverages close to (A) and all show comparable activity as indicated by gamma.

(d) The image-dye hues displayed by the couplers of the present invention are superior to that of (A); all show less unwanted green absorption.

The couplers of the present invention thus exhibit both good photographic activity and dye hue.

EXAMPLE 4

Coatings were made and tested as in Example 4 to compare the performance of coupler (1) of the invention with prior-art couplers (A)-(D). The results are given in Table 4 below.

TABLE 4

| Coup. | laydown mg/m$^2$ | D$_{max}$ | D$_{min}$ | gamma | λ max | Dg(1.0) |
|---|---|---|---|---|---|---|
| 1* | 55 | 2.33 | 0.09 | 3.11 | 436 | 0.23 |
| A* | 55 | 2.38 | 0.10 | 3.08 | 443 | 0.26 |
| C* | 55 | 2.10 | 0.09 | 2.53 | 436 | 0.22 |
| D | 70 | 2.42 | 0.11 | 2.94 |  | 0.24 |
| B | 100 | 2.34 | 0.14 | 2.70 |  | 0.22 |

*with stablizer as in Example 3.

Coupler 1 has a better hue than (A) as shown by $\lambda_{max}$ and Dg, a D$_{max}$ which is comparable or better than the prior couplers (even with (B) and (D) being at higher laydowns), a better of equal D$_{min}$ and a superior contrast to all the prior couplers.

What is claimed is:

1. A color photographic element comprising a support bearing at least one photographic silver halide emulsion layer and a yellow dye-forming coupler represented by the formula:

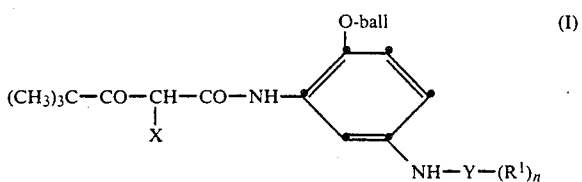

wherein:

R$^1$ is alkyl of 1 to 4 carbon atoms;

ball is a ballast group of such size and configuration as to render the coupler nondiffusible in a photographic element;

Y is CO, PO$_3$ or SO$_2$;

X is an aryloxy coupling-off group; and n is 1 or, when Y is PO$_3$, n is 2.

2. A color photographic element as in claim 1, wherein ball comprises at least one alkyl or aryl moiety.

3. A color photographic element as in claim 1, wherein ball comprises an aryl moiety substituted with at least one alkyl group containing 4 to 10 carbon atoms.

4. A color photographic element as in claim 1, wherein ball is:

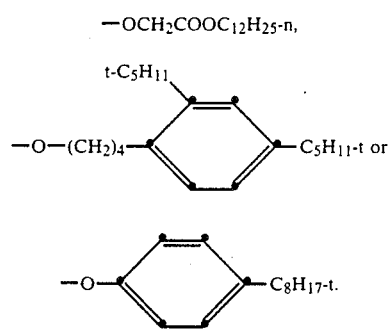

5. A color photographic element as in claim 1, wherein X is a phenoxy group containing electron-withdrawing or -ionizable substituents in at least one of the ortho- and para-positions.

6. A color photographic element as in claim 1 wherein X is:

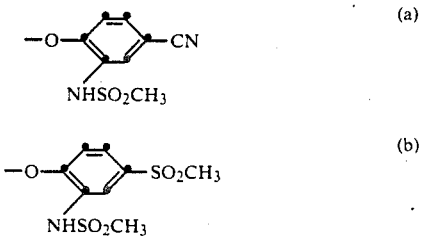

(c) 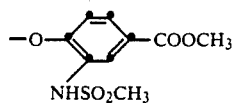

(d) 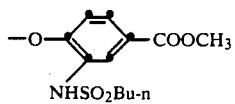

(e) 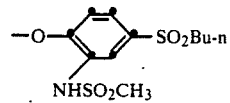

(f) 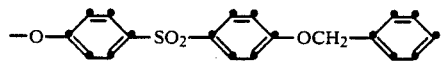

or (g) 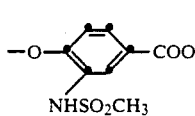

7. A color photographic element as in claim 1, also comprising a blocked bis-phenol dye stabilizer.

8. A color photogrphic element as in claim 1, comprising at least one yellow dye image-forming unit comprised of at least one blue-sensitive silver halide emulsion layer having associated therewith at least one yellow dye-forming coupler as defined in claim 1; at least one magenta dye image-forming unit comprised of at least one green-sensitive silver halide emulsion layer having associated therewith at least one magenta dye-forming coupler; and at least one cyan dye image-forming unit comprising at least one red-sensitive silver halide emulsion layer having associated therewith at least one cyan dye-forming coupler.

* * * * *